United States Patent [19]

Woodard

[11] Patent Number: 5,352,213
[45] Date of Patent: Oct. 4, 1994

[54] INTRAVENOUS FLUID FLOW MONITOR

[76] Inventor: Robert W. Woodard, R.R. 2, Box 94, Frankfort, Kans. 66427

[21] Appl. No.: 153,668

[22] Filed: Nov. 16, 1993

[51] Int. Cl.$^5$ .............................................. A61M 5/00
[52] U.S. Cl. ................................ 604/246; 604/122; 128/DIG. 13; 73/861.52
[58] Field of Search ............... 604/118, 122, 126, 128, 604/129, 246, 251–255, 260; 128/674, DIG. 13; 73/861.49, 861.52, 861.61

[56] References Cited

U.S. PATENT DOCUMENTS

| | | | |
|---|---|---|---|
| 2,140,113 | 12/1938 | Pilling et al. | 604/246 |
| 2,479,786 | 8/1949 | Stevens | 604/246 |
| 2,626,385 | 1/1953 | Schumann | 340/239 |
| 3,001,397 | 9/1961 | Leonard | 604/251 |
| 3,690,312 | 9/1972 | Leibinsohn | 604/118 |
| 3,803,914 | 4/1974 | Noiles | 604/246 |
| 3,929,157 | 12/1975 | Serur | 604/246 |
| 3,963,024 | 6/1976 | Goldowski | 604/254 |
| 4,340,050 | 7/1982 | Noiles | 604/246 |
| 4,425,123 | 6/1984 | DiSalvo | 604/251 |
| 4,511,352 | 4/1985 | Theeuwes et al. | 604/246 |
| 5,098,409 | 3/1992 | Stock | 604/246 |

Primary Examiner—John D. Yasko
Assistant Examiner—Anthony Gutowski
Attorney, Agent, or Firm—Kenneth W. Iles

[57] ABSTRACT

An IV flow monitor is connected to a conventional IV bag via a self-contained puncture tube, and includes a liquid reservoir at the top, which allows the liquid to transfer through a transfer tube and then through a calibrated orifice tube into an orifice chamber, from which the liquid falls through an exit tube connected to a patient or other IV equipment. A manometer tube is connected between the liquid reservoir and the orifice chamber and is aligned with a measurement scale fixed to a backing plate upon which the apparatus is mounted. The pressure drop across the calibrated orifice tube produces a standing column of liquid in the manometer tube and principles of fluid flow allow the rate of flow through the apparatus to be read from the scale. An air trap chamber in an upper portion of the orifice chamber and hydrophobic gas membranes provide safety features that prevent air from being entrained in the liquid flowing through the exit tube to the patient.

20 Claims, 4 Drawing Sheets

INTRAVENOUS FLUID FLOW MONITOR

BACKGROUND OF THE INVENTION

1. Field of the Invention.

The present invention is related to an apparatus and process for measuring the rate of flow of liquid flowing through a conduit. More particularly, the present invention is directed to an apparatus and method for measuring the flow of liquid through an intravenous liquid delivery system into a patient, for monitoring the rate at which the patient is receiving medication, saline solution, or the like.

2. Description of Related Art Including Information Disclosed Under 37 C.F.R. Sections 1.97–1.99.

Two basic types of instruments are now used to measure the flow of liquid in intravenous treatment (IV). First are classes of inexpensive but difficult to use and inaccurate devices such as drip chambers or drip meters. Use of such devices carries a great risk of operator error. Second are sophisticated, expensive electronic devices, that virtually eliminate errors in dosing but can serve only one patient at a time. Using a different meter, or monitor, for each patient greatly increases the expense of using electronic monitors. Often the expense cannot be justified despite the ease of use and accuracy of these electronic monitors.

Therefore a need exists for an inexpensive, reliable IV flow monitor that is simple, easy to manufacture, easy to use and that can be used with more than one patient.

SUMMARY OF THE INVENTION

Accordingly, it is a primary object of the present invention to provide an IV flow monitor that displays the rate of flow of a liquid flowing through the device.

It is another primary object of the present invention to provide an IV flow monitor that displays the rate of flow liquid from a standard IV bag or other container to an intravenously injected patient.

It is another object of the present invention to provide an IV flow monitor that is self-purging or provides ready means of purging excess initial internal air.

It is another object of the present invention to provide an IV flow monitor that includes safety features that prevent any air trapped in the device from being entrained in the exit flow and being carried to the patient during normal use.

It is another object of the present invention to provide an IV flow monitor that is relatively inexpensive to manufacture but that provides reliable monitoring of the rate of flow of IV administered medication to assure proper dosage rate of flow An IV flow monitor according to the present invention can be manufactured as an inexpensive disposable unit or as a reusable unit having certain simple components that can be easily replaced to insure a sterile unit for each patient use. An IV flow monitor according to the present invention can be used with either humans or animals, The IV flow monitor can be manufactured in different sizes to accommodate different ranges of flow rates, e.g., 0–10 ml per hour, 0–100 ml per hour, 0–5,000 ml per hour and so forth.

Two preferred embodiments of the IV flow monitor are disclosed herein. Both embodiments utilize a manometer tube for providing a reading of the liquid flow rate, although the actual use, means of attachment, supporting features and methods of operation all differ significantly from those of prior art manometers.

In prior art manometers, three or four fluids are typically utilized to provide a standing column of liquid in the manometer tube, which is itself adjacent to some type of scale that provides a reading of the flow rate of the measured fluid. Typical those three or four fluids are a liquid in the manometer tube itself, e.g., mercury, the flowing fluid, and an isolating fluid or fluids. When, on typical designs and applications, the rate of flow of the flowing fluid exceeds the designed flow rates that can be measured by the manometer, known as an "overflow" condition, the relationships between the three fluids necessary for accurate operation is sufficiently disrupted that inaccurate readings of flow rate are produced, even after the flow rate of the liquid returns to levels designed to be measured. For example, the manometer liquid typically flows out of the manometer tube during flowing fluid overflow, often through a check valve, or is caught in an overflow basin. This overflow of the manometer liquid results in an inappropriate volume of liquid in the manometer tube and prevents accurate flow rate readings until a worker physically services the manometer by restoring a proper level of liquid to it, emptying the overflow basin, cleaning the check valve, and removing or cleaning all other points where trapped fluid may affect the accuracy of the manometer. This shortcoming makes manometer tubes of the prior art un-useable for use with IV equipment because the labor costs associated with initially setting up the manometer, insuring the correct fluid levels, and an initial manometer zero setting, purging air from the main liquid path and maintaining a sterile field during the process are too expensive and the risk of producing an exit flow with entrained air are too great.

In the present invention the measured fluid and the indicating fluid of the manometer are the same, namely whatever liquid is found in the IV bag being used, with some of the initial sterile air of the device used as the isolating fluid. This unique utilization of the measured liquid to provide the indicating liquid enables the IV flow monitor to by set up and started with only the initial sterile air in the device and the liquid in the IV bag, greatly simplifying start up and use.

The present invention further overcomes obstacles associated with prior art manometer tubes. Prior art manometer tubes do not prevent air or other fluids from being entrained in the main fluid liquid when the measured fluid flow exceeds the maximum design flow rate. An accurate flow rate reading of the prior art manometer can only be restored after a re-purge and start up of the unit. Overflow conditions can occur if the connection of the exit tube to the needle in the patient becomes disengaged due to patient thrashing. If a health care worker reconnects the exit tube to the needle in the patient without first re-purging and restarting the prior art manometer, entrained gases could be carried to the patient, creating a dangerous condition. Likewise, prior are manometers require extensive work for cleaning, purging, filling and zeroing to regain accurate operation after overflow conditions.

These difficulties are overcome by the present invention, in which in one embodiment, an IV flow monitor is provided with a gas permeable hydrophobic membrane in series with the top of the manometer tube and the fluid reservoir. This embodiment self-purging during the normal unrestricted flow condition of start up of current IV devices, and does not allow internal air to become entrained in the exit flow during an overflow condition. Therefore, if the exit tube should happen to become unconnected from the patient, the worker can safely re-connect the exit tube to the patient without purging or otherwise checking the IV flow monitor. Gas permeable hydrophobic membranes are fairly expensive and perhaps not all potential buyers of the present invention will pay the premium price this embodiment may carry.

Therefore, a second preferred embodiment is also disclosed, in which no gas permeable hydrophobic membrane is used at the junction of the manometer tube and the fluid reservoir, but the orifice chamber is altered to act as an air trap chamber in addition to its other functions. The air trap chamber is purged of excess initial air during start up of the IV flow monitor and catches any entrained air in the flowing liquid during operation, preventing any entrained air from reaching the patient. Like the first embodiment, this embodiment allows the health care worker to safely re-connect the exit tube to the needle or the patient without having to re-purge and restart the unit. And this allows the worker to continue to use the IV flow monitor without a purge and re-zeroing of the unit as prior art manometer tubes would require.

Other embodiments are built around these two basic designs. In either case, the IV flow monitors are shipped to the end user filled with sterile air and the IV flow monitors are designed specifically to minimize the set up time and difficulty of use in order to reduce training time and the labor required to use the IV flow monitor, as well as to accelerate adoption of the IV flow monitor.

Other objects and advantages of the present invention will become apparent from the following description taken in connection with the accompanying drawings, wherein is set forth by way of illustration and example, the preferred embodiment of the present invention and the best mode currently known to the inventor for carrying out his invention.

DETAILED DESCRIPTION OF THE PREFERRED EMBODIMENTS

As required by the Patent Statutes and the case law, the preferred embodiments of the present invention and the best mode currently known to the inventor for carrying out the invention are disclosed in detail herein. The embodiments disclosed herein, however, merely illustrate the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus and processes disclosed herein as embodied in any appropriately specific and detailed structure.

Figure 1:
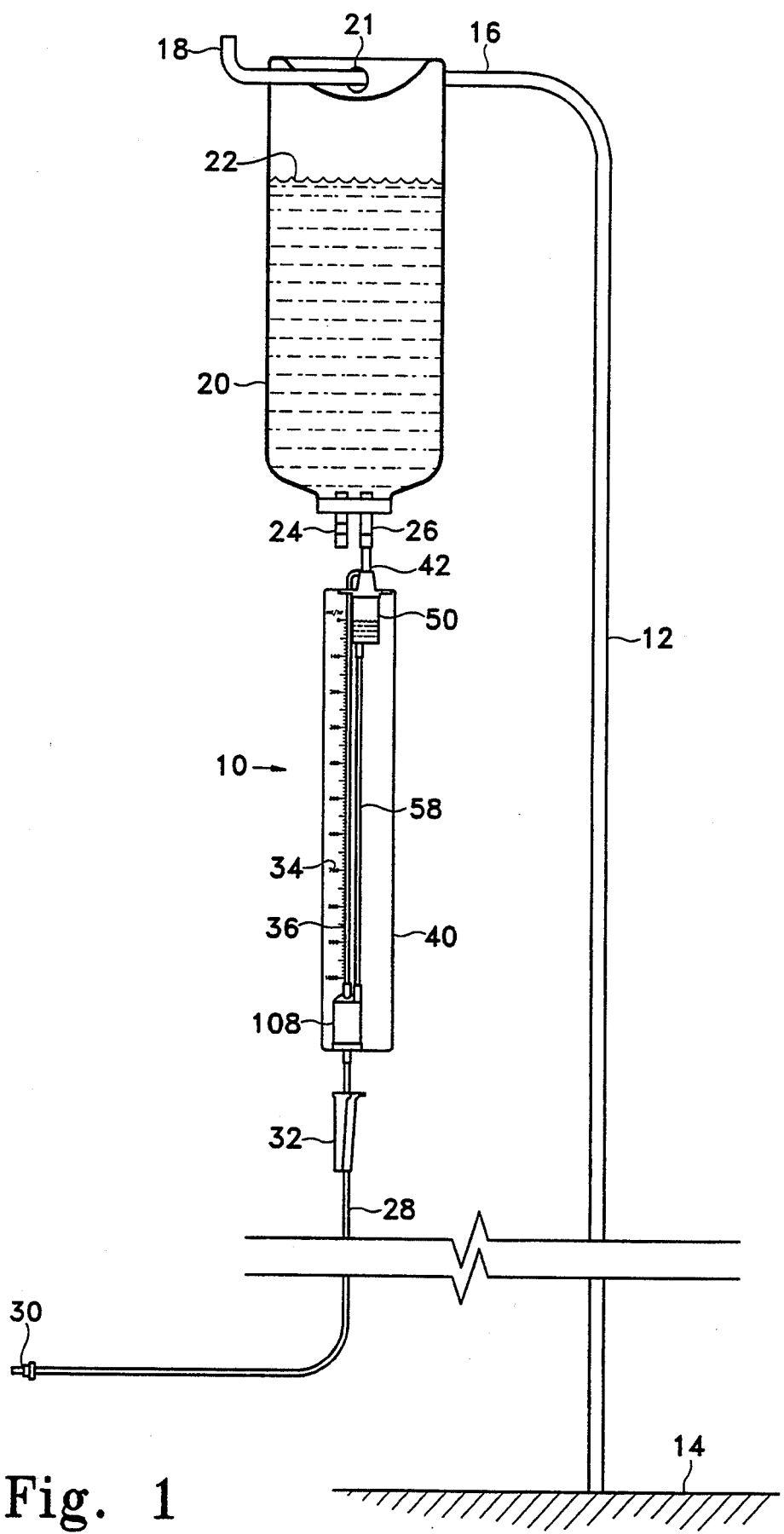
FIG. 1 is front elevation environmental view showing an IV flow monitor according to the present invention as used in conjunction with an IV medicine bag and suitable tubing for delivering the medicine to a patient.
Figure 2:
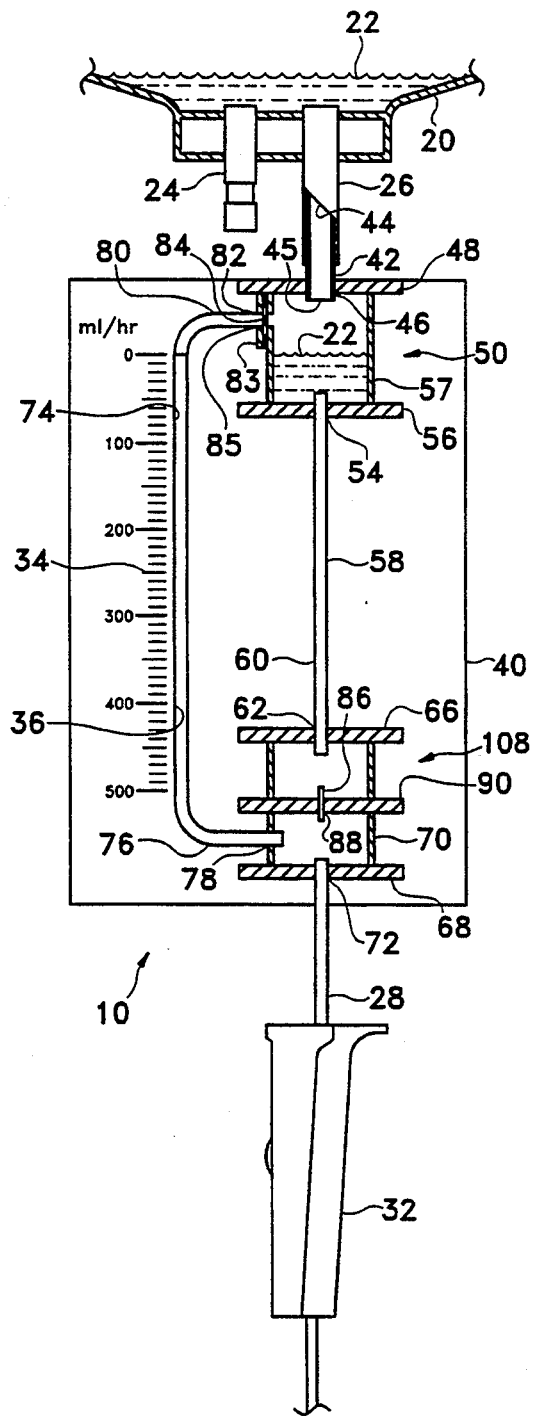
FIG. 2 is a front elevation schematic of an IV flow monitor according to the present invention having a single calibrated orifice tube suspended in a drip or orifice chamber.
Figure 3:
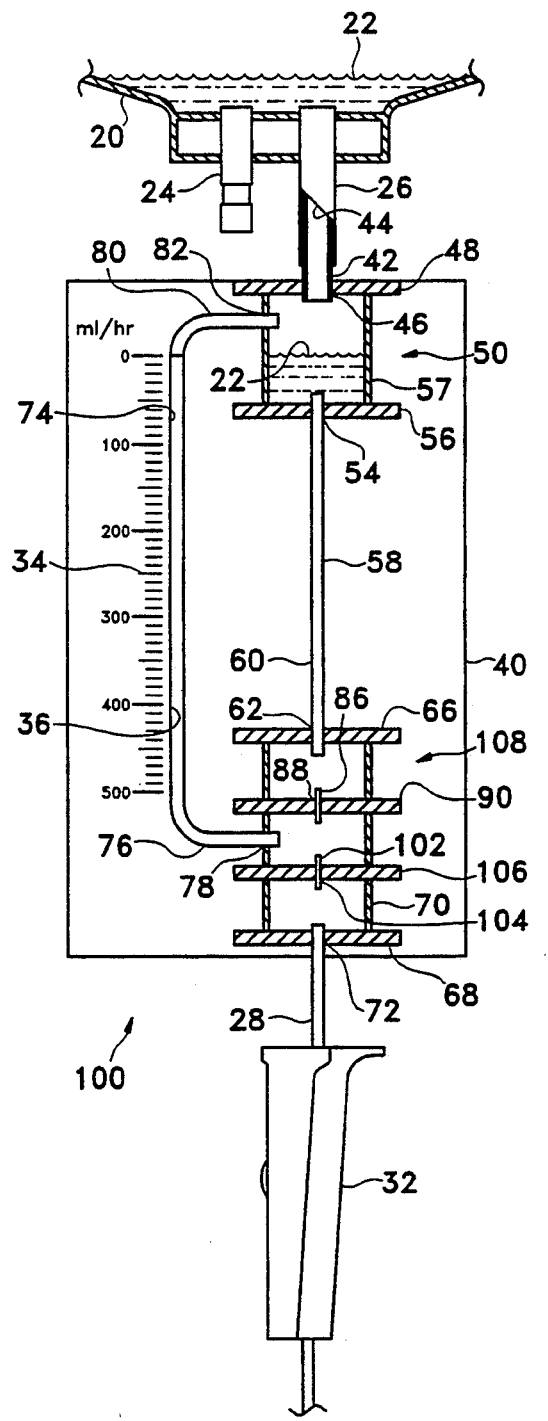
FIG. 3 is a front elevation schematic of an IV flow monitor according to the present invention having two calibrated orifice tubes.

One preferred embodiment of the IV flow monitor disclosed herein utilizes a drip chamber 108 and is illustrated in FIGS. 1, 2, 3. This embodiment does not include any air vent in the drip chamber 108, which includes a calibrated orifice tube 86 for allowing a measured amount of liquid to flow through it under certain head conditions. This embodiment may include an air vent in a fluid reservoir adjacent to the top of a manometer tube 74, (FIG. 1).

The second embodiment, (FIGS. 4-9), unlike the first embodiment, utilizes a portion of the drip chamber as an air trap chamber 109, which carries a calibrated orifice tube 86 seated within it, and further includes an air vent for purging excess air from the air trap chamber 109, as discussed in greater detail below. The air trap chamber 109 traps the required air for correct operation of the IV flow monitor 10 during the start up purge and later catches any air that might become entrained in the liquid flow during normal operation. In certain modifications of this embodiment the air trap chamber 109 includes a gas permeable hydrophobic membrane 116, (FIG. 5), which replaces a vent tube 110, (FIG. 4) and allows any excess air to be vented.

In greater detail, referring now to FIG. 1, there is shown a front elevation of an IV flow monitor 10 according to the present invention set up for use. A stand 12, supported by a floor 14, includes a horizontal arm 16, which terminates in a hook 18. An IV bag 20 includes a mounting aperture 21 near the top of the IV bag 20, which is used for hanging the IV bag 20 on the arm 16, with the hook 18 preventing the IV bag 20 from slipping off the arm 16. The IV bag 20 contains a certain quantity of a desired liquid 22, such as saline solution or medication in solution. A pair of outlet ducts 24, 26 are located in the bottom of the suspended IV bag 20. For use with the present invention, the duct 24 remains sealed at all times. The IV flow monitor 10 is inserted into the duct 26 by a puncture tube 42 (described below) seated in the IV flow monitor 10, which attaches the IV flow monitor 10 to the IV bag 20 and allows the liquid 22 to flow into and through the IV flow monitor 10. An exit tube 28, consisting of a conventional IV tube, is attached the bottom of the IV flow monitor and is routed to a patient (not shown), through a venous access device 30, or other suitable arrangement. A conventional tube clamp 32 on the exit tube 28 allows a patient care worker to control the rate of flow of the liquid 22 into a patient, or to shut-off the flow of liquid 22 through the exit tube 28, as is conventional in the art.

The IV flow monitor 10 includes an appropriate flow rate scale 34, which can be visually read at the convenience of any patient care worker, and a manometer tube 36 for providing a reading of the rate of flow through the IV tubing 28, as described in detail below.

Referring now to FIG. 2, there is shown a front elevation of the IV flow monitor 10, which includes a backing plate 40, upon which the other parts are mounted. The puncture tube 42 includes a sharp point 44 that punctures a seal in the outlet duct 26 of the IV bag 20. The puncture tube 42 includes a proximal end 45 fixed in an aperture 46 in a top wall 48 of a fluid reservoir 50, which is an enclosed sealed volumetric space, except for the opening for the puncture tube 42 and an aperture 54 in a bottom wall 56, which receives a liquid transfer tube 58 and an aperture 82 that receives the manometer tube 82, seated about a hydrophobic gas membrane 84. The fluid reservoir 50 is enclosed by side walls 57. The fluid reservoir 50 may also be made from a single piece by, for example, any of a number of molding processes.

Still referring to FIG. 2, a proximal end 60 of the liquid transfer tube 58 passes through a receiving aperture 62 into the top half of an orifice or drip chamber 108, and is sealed therein. The drip chamber 108 includes a top wall 66, a bottom wall 68, and four side walls 70, (although it may be cylindrical or other shape). The top half of the orifice or drip chamber 108 is an enclosed chamber having two openings for allowing the liquid 22 to flow from the IV bag 20 to the patient, which are the previously mentioned receiving aperture 62 in the top wall 66 and the exit tube 28, seated in an exit tube aperture 72 in the bottom wall 68.

The flow rate scale 34 is either directly formed onto the backing plate 40 by printing, etching, molding or the like, or is a separately printed label or sticker affixed to the backing plate 40. The manometer tube 36 is a U-Shaped tube having a relatively long vertical portion 74, a proximal, (or lower), end horizontal leg portion 76 inserted and sealed in a proximal leg portion receiving aperture 78 in a lower portion of a side wall 70 of the orifice or drip chamber 108, and a distal, (or upper), horizontal leg portion 80 seated about an aperture 82 in a side wall 57 of the fluid reservoir 50. The aperture 82 is covered by a gas permeable hydrophobic membrane 84 forming a covered port at the aperture 82. A plate 83 having an aperture 85 aligned with the aperture 82 seals the membrane 84 in place. The vertical portion 74 of the manometer tube 36 lies along, adjacent to and parallel to the flow rate scale 34.

A calibrated orifice tube 86 is sealed in an aperture 88 through an orifice mounting plate 90, which is seated in the orifice or drip chamber 108 about half-way between the top wall 66 and the bottom wall 68 of the orifice or drip chamber 108. The proximal leg portion 76 of the manometer tube 36 is seated in the drip chamber 108 below the orifice mounting plate 90.

Referring now to FIG. 3, there is shown an alternative embodiment of the IV flow monitor 10, which is identical to the IV flow monitor 10 of FIG. 2 except as described below. The IV flow monitor 10 includes a second limiting orifice, namely second limiting orifice tube 102 seated in an aperture 104 in a second limiting orifice tube mounting plate 106. The limiting orifice tube 102 is directly below the calibrated orifice tube 86. The drip chamber 108 may need to be vertically elongated to accommodate the limiting orifice tube 102 and the mounting plate 106 conveniently.

Further, in the embodiment of FIG. 3, the side walls 57 of the fluid reservoir 50 do not include any type of membrane. The limiting orifice 102 limits the maximum fluid flow through the IV flow monitor 10 so that the maximum pressure drop across the calibrated orifice tube 86 is less than the maximum column height in the manometer tube 36. Then, under unrestricted liquid flow though the exit tube 28, the air in the fluid reservoir 50 and in the manometer tube 36 cannot be pushed into the exit tube 28. Thus, the use of the flow-restricting limiting orifice tube 102 prevents air from being entrained in the liquid 22 flowing through the exit tube 28 to the patient, a crucial feature of any IV device.

Figure 4:
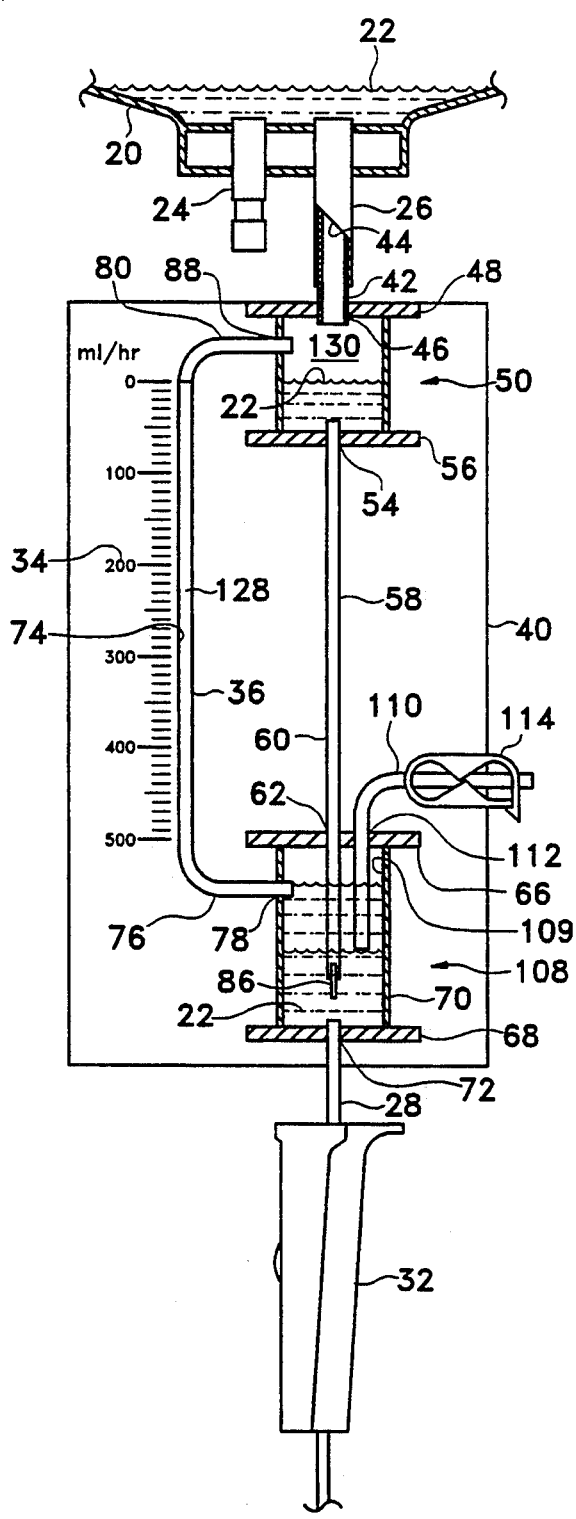
FIG. 4 is a front elevation schematic of another embodiment of an IV flow monitor according to the present invention having a different structure for supporting the calibrated orifice tube and utilizing the drip chamber also as an air trap chamber, which includes an air vent tube.

Referring now to FIG. 4, there is shown another alternative embodiment of the IV flow monitor 10, which is identical to the IV flow monitor of FIG. 2 above, except as described below. The calibrated orifice in the form of a calibrated orifice tube 86 is inserted directly into the proximal end 60 of the liquid transfer tube 58, where it is held in place by frictional engagement, or, if needed, an adhesive. Alternatively, the calibrated orifice in the form of a calibrated orifice tube 86 may be held in any desired vertical orientation by any means, so long as the flowing liquid cannot bypass the orifice tube 86 and the liquid flow is not restricted. The proximal end 60 of the liquid transfer tube 58 is suspended inside a drip or orifice chamber 108 near the bottom wall 68 so that the calibrated orifice tube 86 is immersed in the liquid 22 when the unit is in operation. The upper portion of the orifice chamber 108 above the liquid serves as an air trap chamber 109, which is connected to the outside atmosphere by an air vent tube 110 sealed in an aperture 112 in the top wall 66 of the air orifice chamber 108 and which can be clamped or closed off by a conventional tube clamp 114 after purging. The tube clamp 114 is released, or unclamped, during initial start up purging, allowing excess air to escape, and is clamped to close off the air vent tube 110 after initial start up purging. The normal flow rate through the device does not impact the air level in the air trap chamber 108. Only during overflow conditions, when the air in the top of the fluid reservoir 50 is pushed down the manometer tube and is caught in the air trap chamber 109 does the flow rate affect the level of air in the air trap chamber 109. The sole purpose of the air trap chamber 109 is to catch the air at the top of the fluid reservoir 50 in the event of an overflow condition, which will be pushed down the manometer tube 36, and to hold this air until it can be returned to the top of the fluid reservoir 50 as required for proper operation.

During start up and purge of the IV flow monitor 10 of FIG. 4, some of the initial air in the air trap chamber 109 must be removed, that is, vented to the atmosphere, which can be done via the tube clamp 114, a release plug 126, (FIG. 7), or a gas permeable hydrophobic membrane 116, (FIG. 5), in the air trap chamber 109 or the squeeze type air trap chamber 111, (FIG. 9), or by numerous other less desirable methods, (not shown), depending on the type of design of a particular air trap chamber. During the start up and purge routine, the majority of the air in the whole IV flow monitor 10 resides in the air trap chamber portion of the orifice chamber. After the excess amount of air is purged from the air trap chamber, the majority of air remaining the air trap chamber 108 rises back up to the top of the fluid reservoir 50 after the liquid flow has been shut off, as it normally is, after the start up and purge routine. Because this volume of air directly affects the zero setting of the manometer, it must be tightly controlled. This is accomplished during the purging of the excess air in the air trap chamber 109, (FIG. 5), during the venting process. The correct volume of air is trapped in the air trap chamber 109 when the rising liquid level reaches the height of the bottom of the vent tube 113. Once the liquid 22 level in the orifice chamber 108 has touched the bottom end of the vent tube 113, no more air in the air trap chamber 109 portion of the orifice chamber can be lost out of the vent tube 113.

Figure 5:
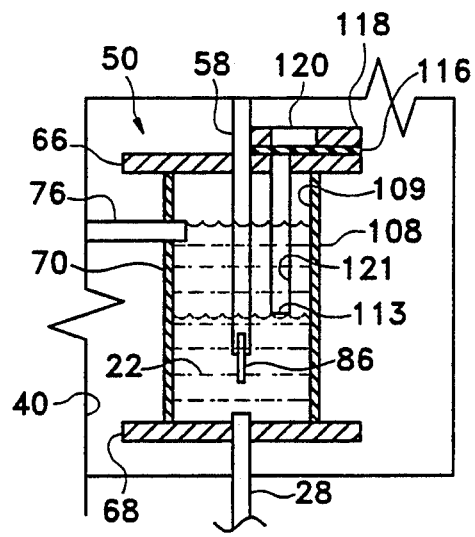
FIG. 5 is an enlarged fragmentary view of an alternative embodiment of the air trap chamber according to FIG. 4 additionally equipped with a gas permeable hydrophobic membrane at the external opening of a vent tube.

Referring now to FIG. 5, there is shown an enlarged fragmentary elevation of the orifice chamber 108 of the IV flow monitor 10 of FIG. 4, having an alternative embodiment of the air vent system described above, in which the clamp 114 has been replaced by a gas permeable hydrophobic membrane 116 held in place by a shield 118 sealingly fixed to an exterior surface of the top wall 66 of the orifice chamber 108 and including an opening 120 exposing the membrane 116 to the outside air.

The embodiment of FIG. 5 is preferred due to simplicity of start up, namely it is only necessary to connect the device of FIG. 5 to an IV bag and allow a free flow of liquid 22 through the IV flow monitor until the liquid 22 that exits from the bottom of the exit tube 28 is free of entrained air and the liquid level in the orifice chamber 108 has reached the bottom end of the vent tube 113. Then the exit tube 28 can be safely connected to the patient and the manometer tube 36 and scale 34 will combine to provide accurate flow rate readings. In the unlikely event of an overflow condition, no air can enter the exit tube 28, as it will automatically be caught in the air trap chamber 109 and no air is vented out of the air trap chamber 109 though the gas membrane until the liquid level in the air trap chamber 109 falls below the bottom of the vent tube 113. This should not occur if the IV flow monitor was purged correctly during start up, as there would not be enough air left in the unit to do this, as it will be automatically caught in the air trap chamber 109 and be returned to the top of the fluid reservoir 50 during the next no flow condition.

Figure 8:
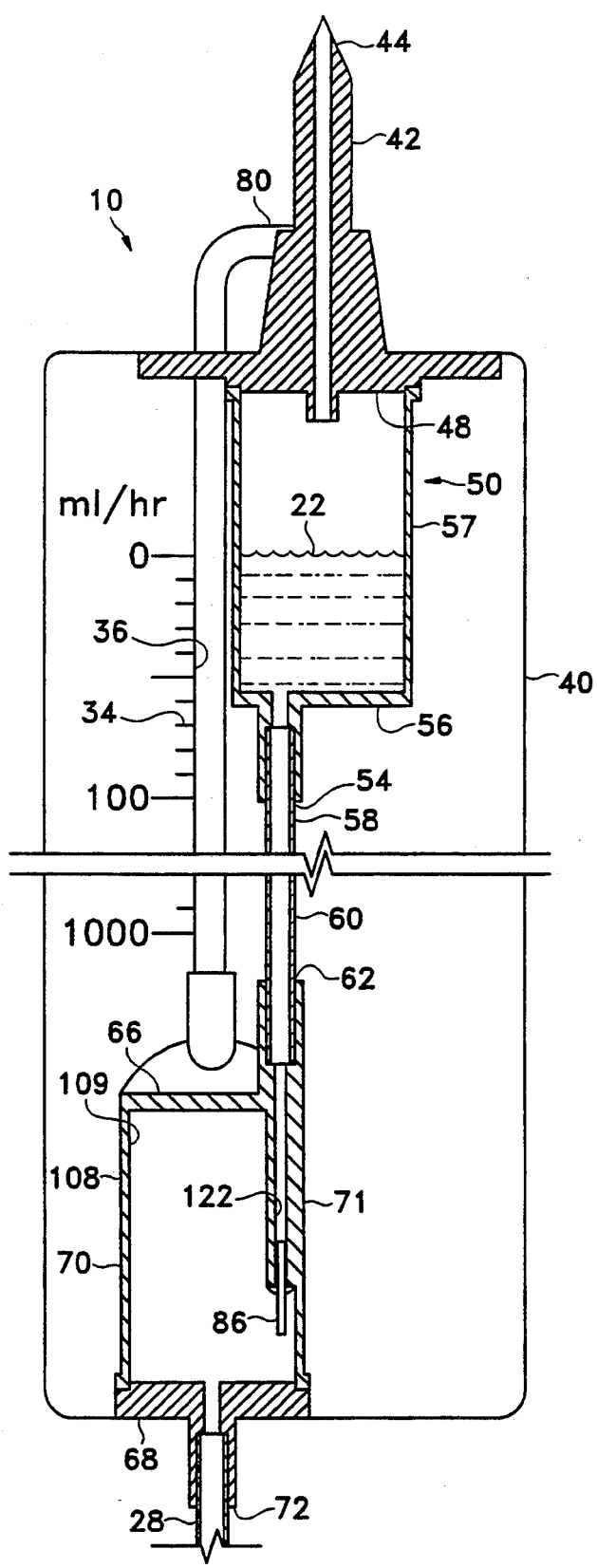
FIG. 8 is a cross section taken along line 8—8 of FIG. 6.

After the start up and purge routine, once the liquid 22 flow out of the IV flow meter 10 has been shut off, the air trapped above the bottom end of the vent tube 113 in the air trap chamber 109 rises to the top of the fluid reservoir 50 through the manometer tube 36. Depending on the geometry of the air trap chamber 109 or 111, a small amount of air may still remain in it, but this is not necessary for correct operation, nor does it impede correct operation. The volume of air that rises form the air trap chamber 109 or 111 to the top of the fluid reservoir 50 must be the same at each start up, but it is also important that this air flow to the top of the fluid reservoir 50 occurs in such a manner that none of it escapes up the puncture tube 42. Any amount lost up the puncture tube 42 would flow into the I.V. bag 20 and the volume of air at the top of the fluid reservoir 50 would cause the zero setting of the manometer tube 36 to be incorrect. This undesirable outcome is prevented in the embodiment of FIG. 8 by offsetting the end of the transfer tube 58 from the center of the fluid reservoir 50 to the right side (as shown in FIG. 8), so it is not under the end of the puncture tube opening. Also the lower end of the puncture tube 42 protrudes slightly into the fluid reservoir 50, or is lower than the inside surface of the top wall 48 of the fluid reservoir 50. These two design features, and the small internal diameter of the puncture tube 42 combine to reduce the possibility that the air in the fluid reservoir 50 will flow up into the puncture tube 42 and into the I.V. bag.

Figure 6:
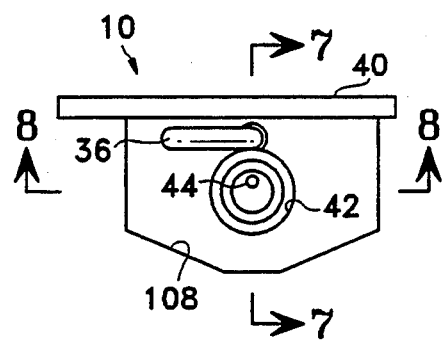
FIG. 6 is a top plan view of a production model of an IV flow monitor according to the present invention.
Figure 9:
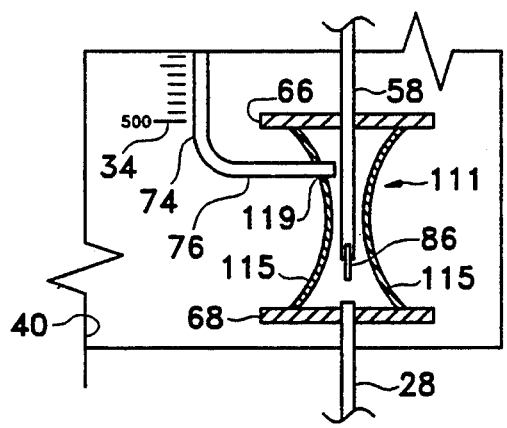
FIG. 9 is a fragmentary view of an IV flow monitor according to the present invention showing an alternative embodiment of an air trap chamber that is flexible and is manually squeezed to purge excess air at system start up, with the air trap chamber shown in the compressed, or squeezed, position with no external venting of the air trap chamber required.
Figure 7:
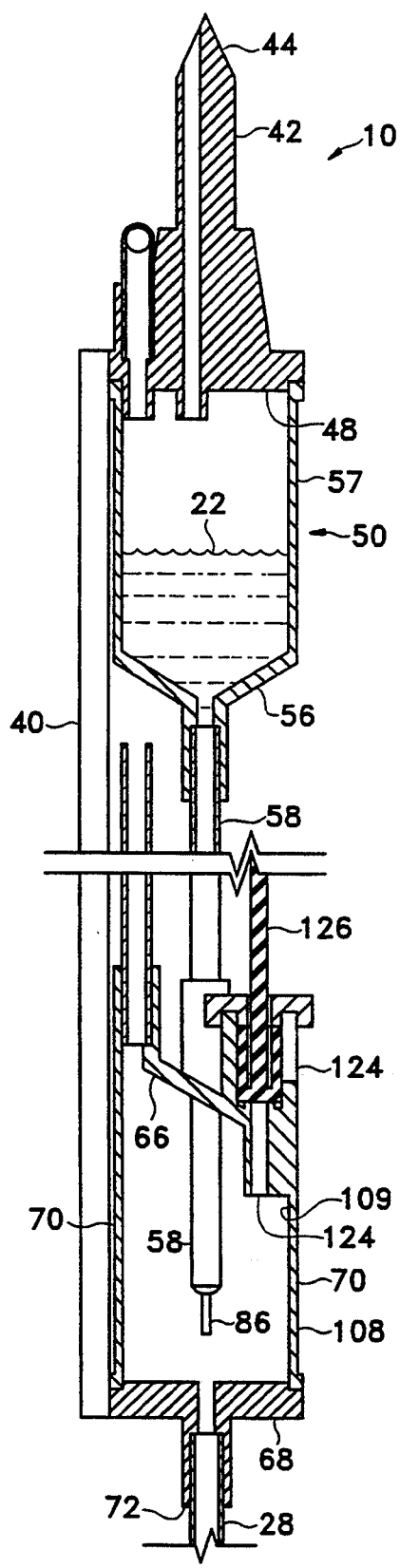
FIG. 7 is a cross section of taken along line 7—7 of FIG. 6.

FIGS. 6, 7 and 8 show the commercial embodiment of the IV flow monitor 10. FIG. 6 is a top plan view of a production model of an IV flow monitor 10 according to the present invention; FIG. 7 is a cross section of taken along line 7—7 of FIG. 6; and FIG. 8 is a cross section taken along line 8—8 of FIG. 6. The air trap chamber 109 includes a thickened side wall 71 having a vertical passage 122 connecting the liquid transfer tube 58 with the metering orifice 86, (FIG. 8). The IV flow monitor 10 also includes an air vent passage 124 into the air trap chamber 109 for venting any excess initial air trapped in the air trap chamber 109 during the purge and start up routine. A release plug 126, which replaces the tube clamp shown in FIG. 4, seals the air vent passage 124 when desired, (FIG. 7). During the purge and start up routine, after all entrained air in the exit tube 28 has been purged, the release plug 126 should be pulled up until liquid 22 flows out of the exit port 124, at which time the release plug should be released, allowing it to spring back to the closed position.

Each embodiment of the IV flow monitor 10 disclosed herein is made from surgical grade flexible tubing, surgical grade stainless steel tubing, and medical grade injection molded plastic components, which are attached, welded, glued, or otherwise fastened together to form the finished product.

The manner of operation of all the embodiments disclosed herein have certain common elements. The puncture tube 42 is inserted into an IV bag 20 containing a desired medical solution, allowing the liquid 22 to flow from the IV bag 20 or other container into and through the IV flow monitor 10.

In normal procedure, the health care worker attaches the IV flow monitor 10 to the IV bag 20 and hangs the IV bag 20 normally. The worker initiates the purge and start up routine by allowing an unrestricted flow of liquid into and out of the IV monitor 10. After there is no longer any sign of entrained air in the exit liquid 22 flow from the exit tube 28, the operator manually vents the excess air out of the air trap chamber 109 by unclamping, unplugging or squeezing the air trap chamber 111, (FIG. 9), as dictated by the specific design. Or, if the air trap chamber 109, 111 includes the hydrophobic gas permeable membrane 116, (FIG. 5), the operator would wait until the liquid level in the orifice chamber 108 rises to the bottom of the vent tube 113.

As a further confirmation of the safe and ready state of the IV flow monitor 10 of FIG. 5, the worker looks through the transparent exit tube 28 to insure that no entrained air bubbles are present in the flowing stream of liquid 22. Then the worker pinches the exit tube 28 closed with the clamp 32, so that no liquid 22 flows out of the tube 28 for a short time to insure that internal fluid levels in the fluid reservoir 50, the orifice chamber 108, the air trap chamber 109, and the manometer tube 36 have reached their proper zero flow equilibrium levels. While the IV flow monitor 10 is in this condition, the worker connects the exit tube 28 to the patient through means of the venous access device 30, (FIG. 1), or to other IV equipment through means well known in the art. The exit tube 28 clamp 32 is then unclasped and adjusted to pinch the exit tube 28 to allow the desired rate of flow, which is a normal technique for currently used IV equipment.

The rate of flow of the liquid 22 into the patient is reflected by the height of liquid 22 in the standing column 128 of liquid 22 produced in the manometer tube 36, (See FIG. 4), and is read from the scale 34. Changes in the flow rate result in corresponding changes in the height of the standing column of fluid in the manometer tube 36, which must, of course, be transparent. The patient care worker can adjust the rate of flow by clamping or pinching the exit tube 28 with the adjustable tube clamp 32 (See, e.g., FIG. 1), as described above. Changes in the downstream flow restrictions or back pressure or a reduction in pressure from the IV bag 20 will change the rate of flow of liquid 22 to the patient and these changes in flow rate are accurately reflected in changes in height of the standing column 128 of liquid 22 in the manometer tube 36, which can then be accurately read from the flow rate scale 34.

The principle of operation of the IV flow monitor 10 is that all liquid 22 flowing through the apparatus to the patient passes through the calibrated orifice 86. A certain pressure applies to liquid above the top, (as viewed in the FIGS.), of the calibrated orifice 86 or 102 and a certain lower pressure applies to liquid below the bottom of the calibrated orifice 86. The pressure drop across the calibrated orifice 86 or 102, (FIG. 3), is used to indicate the rate of flow of the liquid 22 through the apparatus, and hence, into the patient.

Fluid flow through the calibrated orifice 86 can be either laminar or turbulent, depending on the Reynolds number of the fluid in the orifice. The IV flow monitor 10 correctly monitors the flow rate whether the flow through the calibrated orifice 86 is laminar or turbulent, by adjusting the gradations on the flow rate scale 34 in consideration of whether the desired liquid 22 and required size of calibrated orifice or tube 86 will combine to generate a laminar or a turbulent flow. Preferably, however, the orifice in the calibrated orifice tube 86 is of a suitable size to insure laminar flow throughout the intended flow rate range of a specific IV flow monitor 10. In this case, the flow rate scale 34 will be substantially linear, which is easier to read, and therefore less subject to operator error. A linear scale is possible because the flow rate is proportional to the pressure drop when monitoring laminar flow of non-compressible liquids. Using the calibrated orifice tube 86, instead of a simple calibrated orifice in a plate, for example, helps establish and maintain a laminar flow through the pressure drop zone.

In order to achieve an accurate measure of the fluid pressure drop across the calibrated orifice tube 86, which is naturally required to obtain an accurate indication of the rate of flow through the IV flow monitor 10, the air pressure acting on the top of the standing column 128 of liquid 22 in the manometer tube 36 must equal the upstream pressure or head of the fluid flowing through the calibrated orifice or orifice tube 86. To insure this result, the fluid reservoir 50 is required and must be upstream of the calibrated orifice tube 86. The manometer tube 36 is connected to the air space 130, (FIG. 4), at the top of the fluid reservoir 50, allowing the air above the liquid column 128 in the manometer tube 36 to communicate with the air above the fluid reservoir 50.

When no liquid 22 is flowing through the IV flow monitor 10, 100, the standing column 128 has a top level that is the same height as the liquid 22 level in the fluid reservoir 50 because the surface of the air-liquid boundaries are at the same pressure head and the air acting on both liquid surfaces is at the same pressure, requiring the height of both bodies of liquid to be essentially the same. There may be a slight (e.g., <0.127 cm) steady state difference in the steady state height of the liquid 22 in the fluid reservoir 50 due to the difference in diameter of the manometer tube 36 and the diameter of the fluid reservoir 50 and the surface tension of the liquid at the liquid-solid boundary of the liquid 22 and the enclosing container. Use of different material for the fluid reservoir 50 and the manometer tube 136 can contribute to this slight, and harmless, difference in steady heights of the two columns. When, however, fluid flows through the IV flow monitor 10, the resulting pressure drop across the calibrated orifice tube 36 causes the height of the fluid column 128 in the manometer tube 36 to drop to a steady state or equilibrium level proportional to the liquid rate of flow, due to the fluid flow restriction of the calibrated orifice tube 86. Because there is a fixed amount of trapped air volume in the air space 130 at the top of the fluid reservoir 50, and the top of the manometer tube 36, the level of the liquid 22 in the air space 130 rises somewhat as the level of the standing column 128 falls. This effect, however, does not affect the accuracy of the IV flow monitor 10 because any non-linear scaling due to this effect is removed by appropriate calibration of the flow rate scale 34.

The IV flow monitor 10 is provided in a variety of models for measuring flow rates in different ranges. The flow range that a particular model can accurately monitor can be changed by changing the length and internal diameter of the calibrated orifice tube 86, and changing the gradations on the flow rate scale 34. As discussed above, maintaining laminar flow through the calibrated orifice tube 86 under all normal operating parameters is desirable, but if this cannot be done, a combination scale having a non-linear portion to monitor flow rates in non-linear flow portions of the flow range are available. Such scales are constructed to reflect the fact that the pressure drop across the calibrated orifice tube 86 is proportional to the square root of the pressure drop when monitoring turbulent flow of a non-compressible liquid.

The theory of operation of the IV flow monitor 10, 100 is based on certain principles of fluid flow through passages and orifices. When the velocity of a fluid flowing in a tube exceeds a certain critical value that is dependent on the properties of the fluid and the diameter of the tube, describing the flow becomes extremely complicated. Within an extremely thin layer adjacent to the inside walls of the tube, the flow is laminar, but elsewhere the flow is turbulent. At the tube walls, the fluid velocity is zero and that velocity increases uniformly throughout the boundary layer, whose properties are crucial in determining the resistance to flow, among other characteristics not pertinent to the present invention. Beyond the boundary layer, flow is extremely irregular, but exhibits an average forward velocity. Random local currents, or vortices, develop within the fluid, with large increases in the resistance to flow resulting. Experiments have shown that a combination of four factors determine whether the flow of a fluid is laminar or turbulent, and these factors, when combined in a formula, result in the Reynolds number, which is a dimensionless quantity having the same numerical value in any given consistently applied system of measurement. Generally, Reynolds numbers less than about 2,000 indicate a laminar flow, whereas Reynolds numbers greater than about 3,000 indicate a turbulent flow. In the transition region between 2,000–3,000, the flow is unstable and may change from one type to the other. Applying these well-known principles of fluid flow in tubes with specificity allows the sizes of the calibrated orifice tubes 86 and the gradations of the flow rate scales 34 to be determined for any desired reasonable flow range. The task can be simplified by assuming that the liquid 22 is pure water because most IV solutions are overwhelmingly comprised of water with only small amounts of other compounds added. For specific applications involving specific liquids that differ significantly from water, a specific IV flow monitor 10 can be designed and calibrated to insure accurate flow rate readings.

Although the primary purpose of the IV flow monitors 10 disclosed herein is to indicate the rate of flow of IV liquid to a patient, patient safety is a paramount consideration, which has been carefully considered and incorporated into the present invention. Therefore, an IV flow monitor 10 does not include features or operating characteristics that might allow a dangerous condition to occur during use. The IV flow monitor 10 absolutely prevents any air, whether internal or external to the monitor, from becoming entrained or trapped in the exit tube 28 liquid 22 flow stream and carried into the bloodstream of the patient. Currently, IV equipment may require that the initial air in an IV unit be purged by allowing an unrestricted flow of liquid 22 out of the end of the exit tube and by squeezing or venting trapped air out of the IV device prior to connecting the supply tube to a patient. Once an IV device is initially purged of air and connected to a patient, no air can be allowed to enter the stream of IV liquid. Operating an IV unit in abnormal conditions may allow air to enter the system, for example, operating the IV unit in a non-upright position.

In the IV flow monitor 10, without safeguards, it is possible that in some instances air can become entrained in the liquid 22 traveling through the exit tube 28. Such a condition may occur when the actual flow rate exceeds the maximum specified design flow rate of a given model of the IV flow monitor 10, which may cause the pressure drop across calibrated orifice 86 to become larger than the manometer tube 86 will properly register, forcing the standing column 128 of liquid 22 out of the manometer tube 36. Then the air in the air space 130 of the fluid reservoir 50 is pushed into the exit tube 28, where it becomes entrained in the liquid 22 going to the patient. The possibility of this occurrence must be eliminated. Properly monitoring the liquid flow rate, however, requires that some air remains trapped in the air space 130, as discussed above, so the possibility that air from the air space 130 may become entrained in the liquid stream in the exit tube 28 must be addressed by means other than eliminating the air space 130.

This possibility is eliminated by the gas permeable hydrophobic membrane 84 in the embodiment illustrated in FIG. 2. The gas permeable hydrophobic membrane 84 prevents any air from being entrained in the exit tube 28 during overflow conditions. The gas permeable hydrophobic membrane 84 allows air to flow back and forth from the fluid reservoir 50 to the manometer tube 36 as required during normal operation. But in the event of any overflow condition, the gas membrane 84 does not allow liquid 22 to flow out of the fluid reservoir 50 into the manometer tube 36. Therefore, all, or most, of the air is forced out of the fluid reservoir 50 into the manometer tube 36 during overflow conditions, but no liquid 22 would flow into the manometer tube 36 after the air. This keeps the air in the manometer tube 36. If the initial start up routine purges the IV flow monitor 10 with unrestricted flow as required, then any additional volume of air that could not be retained in the manometer tube 36 would already be swept away.

This problem can be solved in a number of different ways. For example, use of the gas permeable hydrophobic membrane 84, (FIG. 1), allows the normal flow of air back and forth across the membrane 84 in response to the changing height of the standing liquid column 128 height in the manometer tube 36, but prevents the flow of liquid from the fluid reservoir 50 into the manometer tube 36 during conditions of excess liquid flow. Normal procedure for purging the IV flow monitor 10, during start up pushes all the air out the fluid reservoir 50 into the manometer tube 36. Excess air then in the manometer tube 36 flows into the exit tube 28 and is then purged from the exit tube 28 in the conventional manner.

Another solution lies in the providing of the air trap chamber as shown in FIGS. 4–8. Excess initial air in the air trap chamber 109, 111 is purged during start up prior to use, that is, such that the volume of air remaining in the air trap chamber 109, 111 is the volume in the top of the fluid reservoir 50 required for accurate usage. The air in the air trap chamber 109 then floats back to the top of the fluid reservoir 50 after all liquid flow out of the IV flow monitor 10 is stopped. If adverse conditions develop during use, any air forced through the manometer tube 36 (as discussed above) is trapped in the air trap chamber 109, where it immediately floats to the top of the liquid 22, and is then returned back to the top of the fluid reservoir once the overflow condition is stopped and corrected. This occurs by simply pinching or shutting the exit tube 28 so that it is completely closed. Once all flow of liquid 22 out of the IV flow monitor 10 has stopped, this trapped air in the air trap chamber 109 flows back up to the top of fluid reservoir 50 by way of the manometer tube 36. Once the air is back at the top of the fluid reservoir 50, the IV flow monitor is again ready for normal operation. Purging any air in the air trap chamber 109 by means of the tube clamp 114, release plug 126, or gas permeable hydrophobic membrane 116 (in the air tap chamber 109, FIG. 5) occurs only once, when the IV flow monitor 10 is first attached to the IV bag 20 during the purge and start up routine after attaching to the IV bag 20.

Alternatively, the air trap chamber 111 is made of a soft, easily squeezed, material, such as flexible plastic, that is squeezed by the worker when air is trapped in it, (FIG. 9), which causes the trapped air to be forced out of the exit tube and carried away during the unrestricted flow purge. The majority of the remaining air rises to the top of the fluid reservoir 50) when the exit tube 28 is pinched shut, as required for the other embodiments using air trap chambers. In this embodiment, the air trap chamber 109 includes flexible side walls 115 made from elastic memory plastic that returns readily to its original shape when force is removed from it and the lower leg portion 76 of the manometer tube 36 is inserted through the aperture 119 in a side wall 115.

The leg portion 76 of the single-piece manometer tube 36 in this embodiment is flexible, and deforms as needed when the air trap chamber 111 is squeezed. When the air trap chamber 111 is released, it fills with liquid 22. Further, the manometer tube 36 may be bent in such a fashion that the lower leg enters the air trap chamber 111 in the middle of the top, minimizing any deflection of the manometer tube 36 during squeezing of the air trap chamber 111.

In the preferred embodiment, the IV flow monitor 10 includes the air trap chamber 109 portion of the orifice chamber 108 and the gas permeable hydrophobic membrane 84 at the junction of the manometer tube 36 and fluid reservoir 50, thereby providing redundant safety features.

When the IV flow monitor is connected to the IV bag 20, as described above, and positioned in the correct upright position, liquid 22 flows from the IV bag 20 into the IV flow monitor 10. With unrestricted flow of liquid 22 out of the exit tube 28, some air is automatically purged back to the IV bag 20 and the some of the air inside the IV flow monitor 10 is purged by flowing through the exit tube 28. Much of the air initially inside the air trap chamber 109, however, remains trapped therein. In order to effectively trap all the air from the top of the fluid reservoir 50 and the manometer tube 36, as described in more detail above, however, the air trap chamber 109 must be nearly filled with liquid 22. Therefore, a means of purging or venting the air inside the air trap chamber 109 to permit most of the orifice chamber 108 to be filled with liquid 22 has been provided. One such means is the air vent tube 110, (FIG. 4), described above. The clamp 114 is unclasped during normal start up procedure to purge the air from the air trap chamber 109. Another such means is the use of the release plug 126, (FIG. 7), which is pulled up during the purge and start up routine to allow air to escape from the air trap chamber 109 via the air vent passage 124, and which is released by the operator after liquid flows out of the port 124, springs closed and remains closed while the liquid 22 is being administered to a patient. Another such means is the provision the gas permeable hydrophobic membrane 116 held in position and protected by the shield 118, (FIG. 5). The latter allows a portion of the initially trapped air to vent to the outside until the fluid level in the air vent tube 121 rises to contact the membrane 116, stopping the flow of fluid.

Maintaining the proper level or amount of air in the air trap chamber 109 is achieved by the extent of penetration of a proximal end 113 of the air vent tube 121, (FIG. 5), into the orifice or drip chamber 108. During the initial venting procedure, liquid displaces the air in the orifice chamber 108 by pushing air out of the air vent tube 113 into the atmosphere. Air is pushed out of the orifice chamber 108 until the liquid 22 level reaches the proximal end, or bottom, of the air vent tube 113. Then any air remaining naturally stays in the air trap chamber 109 portion of the orifice chamber 108 because it cannot escape. The majority of the remaining air then rises back to the top of the fluid reservoir 50 after the exit tube 28 is completely purged and then clamped or pinched shut.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

I claim:
1. An IV flow monitor comprising:

a. a backing plate having an upper end and a lower end;
b. a fluid reservoir fixed to said backing plate and having an inlet;
c. an orifice chamber fixed to said backing plate at a point lower than said fluid reservoir and a calibrated orifice tube mounted within said orifice chamber and means for transferring a liquid from said fluid reservoir through said calibrated orifice tube said orifice chamber having an outlet; and
d. a manometer tube having an upper leg portion, a lower leg portion and a central vertical portion and being in fluid communication with both said fluid reservoir and said orifice chamber and a scale for said manometer tube.

2. An IV flow monitor according to claim 1 further comprising means for connecting said IV flow monitor to an IV bag.

3. An IV flow monitor according to claim 1 further comprising means for delivering a liquid from said IV flow monitor into a patient.

4. An IV flow monitor according to claim 1 wherein an upper portion said orifice chamber further comprises an air trap chamber, and means for selectively venting air from said air trap chamber.

5. An IV flow monitor according to claim 4 wherein said venting means further comprises a vent tube having an upper end and a lower end with said upper end fixed to a vent aperture in an upper portion of said air trap chamber and said lower end of said vent tube is suspended in said orifice chamber at a point that defines a lower boundary of said air trap chamber within said orifice chamber.

6. An IV flow monitor according to claim 5 wherein said venting means further comprises a release plug seated in said vent aperture.

7. An IV flow monitor according to claim 5 wherein said venting means further comprises a gas permeable hydrophobic membrane covering said vent aperture.

8. An IV flow monitor according to claim 5 wherein said venting means further comprises an extension portion of said vent tube external to said orifice chamber and a releasable clamp fastened to said extension portion of said tube.

9. An IV flow monitor according to claim 1 further comprising a gas permeable hydrophobic membrane between said fluid reservoir and said upper leg portion of said manometer tube.

10. An IV flow monitor according to claim 1 further comprising an orifice mounting plate fixed in said orifice chamber at a location between an upper end and a lower end of said orifice chamber and having an aperture therethrough and an orifice tube seated in said aperture.

11. An IV flow monitor according to claim 1 wherein said liquid transfer means further comprises a liquid transfer tube having an upper end seated in an aperture in a lower portion of said fluid reservoir and a lower end suspended within said orifice chamber and said orifice tube fixed in said lower end of said liquid transfer tube.

12. An IV flow monitor according to claim 4 wherein said orifice chamber further comprises a flexible orifice chamber air trap chamber that can be squeezed to exhaust excess air through said air venting means.

13. An IV flow monitor according to claim 1 wherein said central vertical portion of said manometer tube lies adjacent to and parallel to a scale fixed to said backing plate.

14. An IV flow monitor according to claim 1 further comprising an exit tube penetrating said orifice chamber at a point lower than said calibrated orifice tube and means for stopping and starting the flow of a liquid through said exit tube.

15. An IV flow monitor comprising:
 a. a backing plate having an upper end and a lower end;
 b. a fluid reservoir fixed to said backing plate and means for operatively connecting said fluid reservoir to an IV bag;
 c. an orifice chamber fixed to said backing plate at a point lower than said fluid reservoir and including a calibrated orifice tube mounted within said orifice chamber and a liquid transfer tube connected from said fluid reservoir to said orifice chamber said orifice chamber having an outlet; and
 d. a manometer tube having an upper leg portion, a lower leg portion and a central vertical portion and being in fluid communication with both said fluid reservoir and said orifice chamber, and a scale adjacent to and parallel to said central vertical portion of said manometer tube.

16. An IV flow monitor according to claim 15 further comprising a gas permeable hydrophobic membrane between said fluid reservoir and said upper leg portion of said manometer tube.

17. An IV flow monitor according to claim 15 wherein an upper portion said orifice chamber further comprises an air trap chamber, and means for selectively venting air from said air trap chamber.

18. An IV flow monitor comprising:
 a. a backing plate having an upper end and a lower end:
 b. a fluid reservoir fixed to said backing plate and means for operatively connecting said fluid reservoir to an IV bag;
 c. an orifice chamber fixed to said backing plate at a point lower than said fluid reservoir and including a calibrated orifice tube mounted within said orifice chamber and a liquid transfer tube connected from said fluid reservoir to said orifice chamber, wherein an upper portion said orifice chamber further comprises an air trap chamber, and means for selectively venting air from said air trap chamber said orifice chamber having an outlet; and
 d. a manometer tube having an upper leg portion, a lower leg portion and a central vertical portion and being in fluid communication with both said fluid reservoir and said orifice chamber, and a scale adjacent to and parallel to said central vertical portion of said manometer tube.

19. An IV flow monitor according to claim 18 further comprising an orifice mounting plate fixed in said orifice chamber at a location between an upper end and a lower end of said orifice chamber and having an aperture therethrough and an orifice tube seated in said aperture.

20. An IV flow monitor according to claim 18 wherein said venting means further comprises a vent tube having an upper end and a lower end with said upper end fixed to a vent aperture in an upper portion of said air trap chamber and said lower end of said vent tube is suspended in said orifice chamber at a point that defines a lower boundary of said air trap chamber within said orifice chamber.

* * * * *